（12）United States Patent
Ganapathy et al.

(10) Patent No.: US 8,309,534 B2
(45) Date of Patent: Nov. 13, 2012

(54) COMPOSITIONS COMPRISING A GPR109 LIGAND FOR TREATING DISORDERS OF THE DIGESTIVE TRACT AND/OR CANCER

(75) Inventors: Vadivel Ganapathy, Martinez, GA (US); Puttur D. Prasad, Martinez, GA (US); Muthusamy Thangaraju, Evans, GA (US); Gail Cresci, Augusta, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 252 days.

(21) Appl. No.: 12/599,923

(22) PCT Filed: May 15, 2008

(86) PCT No.: PCT/US2008/063752
§ 371 (c)(1),
(2), (4) Date: Nov. 12, 2009

(87) PCT Pub. No.: WO2008/144423
PCT Pub. Date: Nov. 27, 2008

(65) Prior Publication Data
US 2010/0137236 A1 Jun. 3, 2010

Related U.S. Application Data

(60) Provisional application No. 60/930,237, filed on May 15, 2007.

(51) Int. Cl.
*A01N 43/04* (2006.01)
*A61K 31/70* (2006.01)
(52) U.S. Cl. ............. 514/49; 514/43; 514/784; 514/785
(58) Field of Classification Search .................. None
See application file for complete search history.

(56) References Cited

U.S. PATENT DOCUMENTS
2003/0032672 A1  2/2003 Kim et al.

FOREIGN PATENT DOCUMENTS
| WO | WO 00/56153 | 9/2000 |
| WO | WO 02/085400 | 10/2002 |
| WO | WO 2005/011677 | 2/2005 |
| WO | WO 2005/016870 | 2/2005 |
| WO | WO 2007/027661 | 3/2007 |

OTHER PUBLICATIONS

Chapman et al. Cancer Research (1954), vol. 14, pp. 372-376.*
Arora, "Rationale for the use of nicotinic acid and its amide in non-pellagrous diarrhea and psychoneurosis," *The Antiseptic*, 49(6): 442-7 (1952).
Butzner, et al., "Butyrate enema therapy stimulates mucosal repair in experimental colitis in the rat," *Gut*, 38: 568-73 (1996).
Cresci, et al., "Colonic gene expression in conventional and germ-free mice with a focus on the butyrate receptor GPR109A and the butyrate transporter SLC5A8," *J. Gastrointest. Surg.*, 14: 449-461 (2010).
Hamer, et al., "The role of butyrate on colonic function," *Alimentary Pharmacol. and Ther.*, 27:104-119 (2008).
Hoshimoto, et al., "Caprylic acid and medium-chain tryglycerides inhibit IL-8 gene transcription in Caco-2 cells: comparison with the potent histone deacetylase inhibitor trichostatin A," *Br. J. Pharmacal.*, 136: 280-6 (2002).
Knowles, et al., "Niacin induces activation in macrophages via HM74 and HM74a-mediated induction of prostaglandin synthesis pathways," *Biochem. Pharmacal.*, 71(5): 646-56 (2006).
National Center for Biotechnology Information "Accession No. NM_177551," G protein-coupled receptor 109A, updated Feb. 2, 2010 (accessed Feb. 18, 2010).
National Center for Biotechnology Information "Accession No. NM_006018," G protein-coupled receptor 109B, updated Feb. 7, 2010 (accessed Feb. 18, 2010).
Soudijn, et al., "Nicotinic acid receptor subtypes and their ligands," *Med. Res. Rev.*, 27(3): 417-33 (2007).
Taggart, et al., "(D)-β-Hydroxybutyrate inhibits adipocyte lipolysis via the nicotinic acid receptor Puma-G," *J. Biol. Chem.*, 280(29): 26649-52 (2005).
Thangaraju, et al., "GPR109A is a G-protein-coupled receptor for the bacterial fermentation product butyrate and functions as a tumor suppressor in colon," *Cancer Res.*, 69(7): 2826-32 (2009).
Wufka, et al., "The IFNγinducible G-protein coupled receptor Puma-G is a regulator of intracellular cAMP levels in macrophages and may play a role in tumor formation," abstract only, *Immunology*, 210(6-8): 396 (2005) and Joint Annual Meeting of the German and Scandinavian Societies of Immunology; Kiel, Germany, Sep. 21-24, 2005.

* cited by examiner

Primary Examiner — Patrick Lewis
(74) Attorney, Agent, or Firm — Pabst Patent Group LLP (57) ABSTRACT

Pharmaceutical compositions containing an effective amount of a ligand for GPR109 to decrease intracellular cAMP levels of a subject in combination with an effective amount of a DNA methyl transferase inhibito to reduce or inhibit down-regulation of GPR109 in the intestinal epithelial cells of the subject relative to a control are provided. It has been discovered that ligands for GPR109 can be used to treat one or more symptoms of cancer, inflammatory disorders, and diarrhea. Representative CPR109 ligands include, but are not limited to butyrate, β-hydroxybutyrate, nicotinic acid, acifran, and octanoate. Suitable DNA methyl transferase inhibitors include 5-azacytidine, 5-aza-2'-deoxytidine, 1-β-D-arabin-farnosyl-5-azacytosine and dihydro-5-azacytidine. Typically, the compositions are formulated to achieve a GPR109 ligand serum blood level of about 1 to about 1000 μM. The compositions are useful for the treatment of one or more symptoms of cancer. Preferred cancers that can be treated using the disclosed compositions include, but are not limited to colon cancer, breast cancer and leukemia. Methods for treating cancer, inflammatory disorders, and diarrhea are also provided.

16 Claims, 5 Drawing Sheets

COMPOSITIONS COMPRISING A GPR109 LIGAND FOR TREATING DISORDERS OF THE DIGESTIVE TRACT AND/OR CANCER

CROSS-REFERENCE TO RELATED APPLICATIONS

This application is a filing under 35 U.S.C. §371 of PCT/US2008/1063752 filed with the U.S. Receiving Office of the Patent Cooperation Treaty on May 15, 2008, which claims benefit of and priority to U.S. Provisional Patent Application No. 60/930,237, filed on May 15, 2007, and where permissible is incorporated herein in its entirety.

FIELD OF THE INVENTION

The invention is generally related to pharmaceutical compositions and methods of treating disorders of the digestive tract, in particular inflammatory disorders, cancer, and diarrhea.

BACKGROUND OF THE INVENTION

Diarrhea and inflammatory gut disorders are a major and increasing health cost in the US and other countries. Inflammatory bowel disease (IBD) affects an estimated 600,000 Americans a year. IBD commonly refers to ulcerative colitis (UC) and Crohn's disease (CD), which are chronic inflammatory diseases of the gastrointestinal tract of unknown etiology. Crohn's disease is also referred to as regional enteritis, terminal ileitis, or granulomatous ileocolitis. Increasing evidence suggests that, at least in CD, there is a defect in the function of the intestinal immune system. As a consequence, there is a breakdown of the defense barrier of the gut, which, in turn, results in exposure of the mucosa to microorganisms or their products. The result is a chronic inflammatory process mediated by T cells.

Inflammation normally is a localized, protective response to trauma or microbial invasion that destroys, dilutes, or walls-off the injurious agent and the injured tissue. It is characterized in the acute form by the classic signs of pain, heat, redness, swelling, and loss of function. Microscopically, it involves a complex series of events, including dilation of arterioles, capillaries, and venules, with increased permeability and blood flow, exudation of fluids, including plasma proteins, and leukocyte migration into the area of inflammation.

Other diseases of the gastrointestinal tract also have an enormous impact on health. According to the American Cancer Society 154,000 new cases of colorectal cancer will be diagnosed in the U.S. in 2007. With an average cost of between $35,000 and $80,000 for direct medical care for each cancer episode, total cost for treatment of anticipated new cases in 2007 is estimated at $8.3 billion. Thus, there is a need for new and effective treatments for gastrointestinal disorders.

It is an object of the invention to provide compositions and methods for the treatment of one or more symptoms of a disorder of the gastrointestinal tract.

It is another object of the invention to provide compositions and methods for the treatment of cancer.

It is still another object of the invention to provide compositions and methods for inflammatory disorders.

It is yet another object of the invention to provide compositions and methods for treating diarrhea.

SUMMARY OF THE INVENTION

Pharmaceutical compositions containing an effective amount of a ligand for GPR109 to decrease intracellular cAMP levels of a subject in combination with an effective amount of a DNA methyl transferase inhibitor to reduce or inhibit downregulation of GPR109 in the intestinal epithelial cells of the subject relative to a control are provided. It has been discovered that ligands for GPR109 can be used to treat one or more symptoms of cancer, inflammatory disorders, and diarrhea. Representative GPR109 ligands include, but are not limited to butyrate, β-hydroxybutyrate, nicotinic acid, acifran, and octanoate. Suitable DNA methyl transferase inhibitors include 5-azacytidine, 5-aza-2'-deoxytidine, 1-β-D-arabinfumosyl-5-azacytosine and dihydro-5-azacytidine. Typically, the compositions are formulated to achieve a GPR109 ligand serum blood level of about 1 to about 1000 µM. The compositions are useful for the treatment of one or more symptoms of cancer. Preferred cancers that can be treated using the disclosed compositions include, but are not limited to colon cancer, breast cancer and leukemia.

One embodiment provides a method for treating one or more symptoms of cancer by administering to a subject and effective amount of a DNA methyltransferase inhibitor to induce expression of GPR109 in cells of the subject, in combination with an effective amount of a GPR109 ligand to decrease intracellular levels of cAMP in the cells induced to express GPR109. In another embodiment, the DNA methyltransferase is administered and the GPR109 ligand is administered after the DNA methyltransferase.

Still another embodiment provides a method for treating an inflammatory disorder by administering to a subject an effective amount of a GPR109 ligand to reduce intracellular cAMP in the subject. Preferred inflammatory disorders include inflammatory bowel disease, necrotizing enterocolitis and lung inflammation.

Yet another embodiment provides a method for treating diarrhea by administering to a subject an effective amount of a GPR109 ligand to decrease intracellular cAMP levels in intestinal epithelial cells of the subject.

BRIEF DESCRIPTION OF THE DRAWINGS

FIG. 2B is bar graph of NF-κB activity×$10^4$ in KM12L4 cells plus vector treated with butyrate, nicotinate, acifran, or 1-isopropyl-benzotriazole-5-carboxylic acid) in the presence or absence of lipopolysaccharide. FIG. 2C is bar graph of NF-κB activity×$10^4$ in transfected with GPR109A treated with butyrate, nicotinate, acifran, or 1-isopropyl-benzotriazole-5-carboxylic acid) in the presence or absence of lipopolysaccharide. FIG. 2D shows a gel of RT-PCR products of GPR109A or HPRT1 in HCT116 cells or HCT116-DNMT1$^{-/-}$. FIG. 2E is bar graph of NF-κB activity×$10^4$ in HCT116 cells treated with butyrate, nicotinate, acifran, or 1-isopropyl-benzotriazole-5-carboxylic acid) in the presence or absence of lipopolysaccharide. FIG. 2F is bar graph of NF-κB activity×$10^4$ in HCT116-DNMT1$^{-/-}$ cells treated with butyrate, nicotinate, acifran, or 1-isopropyl-benzotriazole-5-carboxylic acid) in the presence or absence of lipopolysaccharide.

FIG. 4B shows semi-quantitative RT-PCR for GPR109A mRNA in normal colon (NCM460 and CCD841) and colon cancer (SW480, SW620, KM12C, KM12L4, HT29, HCT116, Colo201, Colo205, and Ls174T) cell lines after treatment with or without 5'-azacytidine (2 µg/ml; 72 h). FIG. 4C shows steady-state levels of DNMT1, DNMT3a, and DNMT3b mRNA in normal colon cell lines and cancer colon cell lines. FIG. 4D shows steady-state levels of mRNAs for DNMT1, DNMT3a, DNMT3b, and HPRT1 in normal human colon tissues and in human colon cancer tissues by semi-quantitative RT-PCR. FIG. 4E shows expression levels of DNMT1, DNMT3a, and DNMT3b mRNA and expression levels of GPR109A and GPR109B mRNA in HCT116 cell line (a human colon cancer cell line) and in isogenic cell lines with the deletion of DNMT1, DNMT3b, or both (DKO). FIG. 4F the expression of GPR109A in SW480, HCT116, or KM121C cells treated with or without procainamide.

FIG. 6B shows RNA levels for the identified death receptor-related genes in KM12L4 cells transfected with either pcDNA or GPR109A cDNA, followed by treatment with or without nicotinate (0.5 mM) for 24 h. FIG. 6C shows RNA levels for the identified death receptor-related genes in KM12L4 cells transfected with either pcDNA or GPR109A cDNA, followed by treatment with or without nicotinate (0.5 mM) for 24 h. Total RNA was extracted from these cells and semi-quantitative RT-PCR was carried out using primers specific for the cell cycle-related genes.

DETAILED DESCRIPTION OF THE INVENTION

I. Definitions

Unless otherwise defined, all technical and scientific terms used herein have the same meaning as commonly understood by one of ordinary skill in the art to which this invention pertains. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "DNA methylation inhibitor" is used interchangeably with DNA methyl transferase inhibitor and refers to compounds that inhibit the methylation of DNA. Representative DNA methylation inhibitors include, but are not limited to 5-azacytidine, 5-aza-2'-deoxytidine, 1-β-D-arabinfurnosyl-5-azacytosine and dihydro-5-azacytidine.

The term "effective amount" or "therapeutically effective amount" means a dosage sufficient to provide treatment of the inflammatory disorder, cancer or diarrhea or disease state being treated or to otherwise provide a desired pharmacologic and/or physiologic effect. The precise dosage will vary according to a variety of factors such as subject-dependent variables (e.g., age, immune system health, etc.), the disease, and the treatment being effected.

The terms "individual," "individual," "subject," and "patient" are used interchangeably herein, and refer to a mammal, including, but not limited to, rodents, simians, humans, mammalian farm animals, mammalian sport animals, and mammalian pets.

As used herein, the term "treating" includes alleviating, preventing and/or eliminating one or more symptoms associated with inflammatory disorders, cancer or diarrhea.

The term "reduce", "inhibit" or "decrease" are used relative to a control. Controls are known in the art. For example a decrease response in a subject or cell treated with a compound is compared to a response in subject or cell that is not treated with the compound.

II. Compositions for Treating Cancer

A. GPR109

GPR109 is a G-protein-coupled receptor associated with Gi. Gi inhibits the production of cAMP. Thus, activation of GPR109 results in the decrease of intracellular levels of cAMP. It has been discovered activation of GPR109 offers protection against disorders of the gastrointestinal tract. Accordingly, one embodiment provides compositions for treating one or more symptoms of a gastrointestinal disorder wherein the compositions include one or more ligands for GPR109 and optionally at least one additional therapeutic agent. Representative disorders that can be treated with the disclosed compositions include, but are not limited to cancer, inflammation, and diarrhea. Specific cancers that can be treated include, but are not limited to colon cancer, breast cancer, and leukemia. Representative inflammatory disorders that can be treated include, but are not limited to inflammatory bowel disease (IBD) including ulcerative colitis and Crohn's, necrotizing enterocolitis, as well as lung inflammation.

Mouse and rat have only one gene coding for this G-protein-coupled receptor. The rodent form is known as PUMA-G (Protein upregulated in macrophages by interferon-gamma). The general nomenclature for this receptor protein is GPR109. Humans have two genes coding for highly homologous receptor proteins. According to Human Genome Nomenclature, these two genes are known as GPR109A (NCBI Accession No. NM__177551) and GPR109B (NCBI Accession No. NM__006018). The rodent PUMA-G and the human GPR109A show similar ligand specificity, and therefore the human GPR109A is homologous to rodent receptor PUMA-G.

The human-specific GPR109β isoform shows different ligand specificity and does not interact with niacin and beta-hydroxybutyrate. These two compounds are the ligands for GPR109A and PUMA-G. In fact, PUMA-G/GPR109A was discovered when investigators were looking for the mechanism underlying the anti-lipolytic actions of niacin.

PUMA-G/GPR109A is expressed abundantly in adipocytes and this explains the pharmacologic actions of this receptor in eliciting the anti-lipolytic effects. Activation of the receptor with niacin reduces intracellular cAMP levels in adipocytes which then inactivates the hormone-sensitive lipase and thus reduces lipolysis and the release of free fatty acids into blood. The receptor is also expressed in immune cells, but the physiologic function in these cells is not known. A recent study showed that butyrate is also a ligand for PUMA-G/GPR109A, but the affinity is very low. Concentrations of about 2 mM are needed to elicit half-maximal activation of the receptor.

Butyrate is present at high levels (~20 mM) in the colon and this concentration is sufficient to activate the receptor maximally. Niacin and beta-hydroxybutyrate are not present in the colonic lumen. Therefore, butyrate is likely the only physiologic ligand for the receptor in the colon. It was also discovered that the GPR109A and B receptors are expressed abundantly in the colon as well as in the terminal part of the small intestine It has also been discovered that GPR109A mediates inhibitory effects of butyrate on LPS-induced activation of NF-κB promoter in colonic epithelial cells and that SLC5A8 mediates the inhibitory effects of butyrate on dendritic cell maturation. Both these effects are directly relevant to NEC. An abnormal immune function with an inappropriate and heightened response to commensal bacteria in the ileum/colon underlies the cause of NEC. The bacterial metabolite butyrate suppresses the response of the gut-associated lymphoid tissue to commensal bacteria. The ability of butyrate to suppress the induction of NF-κB by bacterial LPS in the colon and to block the maturation of dendritic cells provides a mechanism for the anti-inflammatory effects of butyrate. The butyrate receptor GPR109A and the butyrate transporter SLC5A8 mediate these effects. These two proteins are located in the apical membrane of the intestinal/colonic epithelial cells and on the immune cells, ideally suited to transduce the effects of butyrate produced in the lumen. Therefore, provision of butyrate in the intestinal/colonic lumen would be a logical therapy for the prevention of NEC.

One embodiment provides compositions for the treatment of inflammatory disorders including one or more ligands for GPR109. The ligand can be specific for GPR109A, GPR109B, or both. Certain compositions contain a ligand specific for GPR109A and a ligand specific for GPR109B. The compositions can also include one or more additional therapeutic agents. Compositions for treating inflammatory disorders of the gut can include anti-inflammatory agents, anti-spasmotics.

B. Ligands of GPR109

In a preferred embodiment, the disclosed compositions include one or more ligands of GPR109 or derivatives thereof. Derivatives include ligands that have been chemically modified to increase bioavailability, absorption, solubility, or potency. Representative ligands of GPR109A include, but are not limited to beta-hydroxybutyrate, niacin (also referred to as nicotinic acid or nicotinate), and butyrate. A representative ligand for GPR109B includes but is not limited to octanoate.

C. Pharmaceutical Compositions

The disclosed compositions containing one or more ligands of GPR109 can be formulated as pharmaceutical compositions. The pharmaceutical compositions may be for administration by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in unit dosage forms appropriate for each route of administration.

1. Formulations for Parenteral Administration

In one embodiment, the compositions are administered in an aqueous solution, by parenteral injection. The formulation may also be in the form of a suspension or emulsion. In general, pharmaceutical compositions are provided including effective amounts of a GPR109 ligand and one or more DNA methylation inhibitor, or derivative products, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Enteral Administration

The compositions can be formulated for oral delivery. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions (as, for example, proteinoid microspheres reported in U.S. Pat. No. 4,925,673). Liposomal encapsulation may be used and the liposomes may be derivatized with various polymers (e.g., U.S. Pat. No. 5,013, 556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The GPR109 ligand or DNA methylation inhibitor may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The GPR109 ligand and one or more DNA methylation inhibitor can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e. the drug is enclosed in a semipermeable membrane which allows water to enter and push drug out through a single small opening due to osmotic effects. For oral formulations, the location of release may be the stomach, the small intestine (the duodenum, the jejunem, or the ileum), or the large intestine. Preferably, the release will avoid the deleterious effects of the stomach environment, either by protection of the peptide (or derivative) or by release of the peptide (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HP-MCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

3. Controlled Delivery Polymeric Matrices

Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of GPR109 ligands and one or more DNA methylation inhibitor, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release 5, 13-22 (1987); Mathiowitz, et al., Reactive Polymers 6, 275-283 (1987); and Mathiowitz, et al., J. Appl. Polymer Sci. 35, 755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

4. Dosages

For all of the disclosed compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 100 mg/kg of body weight daily are administered to mammals. Generally, for intravenous injection or infusion, dosage may be lower. Preferably, the compositions are formulated to achieve a GPR109 ligand serum level of about 1 to about 1000 µM.

D. Combination Therapy

The disclosed compositions can be administered alone or in combination with one or more additional therapeutic agents. For compositions for treating cancer, a preferred additional therapeutic agent is a DNA methylase inhibitor. Representative DNA methylase inhibitors include, but are not limited to 5-azacytidine, 5-aza-2'-deoxytidine, 1-β-D-arabin-fumosyl-5-azacytosine, dihydro-5-azacytidine or combinations thereof.

The disclosed compositions can be administered with an antibody or antigen binding fragment thereof specific for a growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-1receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor eceptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Ax1; RYK; DDR; and Tie.

Additional therapeutic agents include conventional cancer therapeutics such as chemotherapeutic agents, cytokines, chemokines, and radiation therapy. The majority of chemotherapeutic drugs can be divided in to: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the new tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

Other suitable therapeutics include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflorasone diacetate, fluradrenolone acetonide, medrysone, amcinafel, ameinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

III. Methods of Treatment

A. Cancer

The disclosed compositions can be used to treat cancer. It was discovered that GPR109A expression was reduced in cancer cells compared to normal tissue. The decrease in mRNA levels was about 85%. That is, the expression of GPR109A is only about 15% in cancer tissue compared to normal tissue. Interestingly, the expression of GPR109B is reduced in cancer only by about 25%. Since GPR109A is homologous to PUMA-G, the expression of PUMA-G in a mouse model of intestinal/colon cancer was examined. The expression of PUMA-G is reduced markedly (by more than 90%) in tumor tissues from the mouse compared to normal tissue.

The expression of GPR109A and GPR109B in a number of human colon cancer cell lines (nine in total) was examined and compared the expression with that in non-transformed colon cell lines (2). Except for one, in all the remaining 8 cancer cell lines, GPR109A is expressed at very, very low levels compared to non-transformed cell lines. Again, the expression of GPR109B is not affected in cancer cell lines to any significant extent. These data with cell lines corroborate those with primary cancer in colon.

The decrease in the expression of GPR109A in colon cancer is the result of DNA methylation. When colon cancer cell lines are treated with 5-azacytidine, a demethylating agent, the expression of the gene is induced. This hypermethylation of the gene in colon cancer is due to cancer-associated increase in the expression of DNMTs (DNA methyltransferases) and in the expression of the oncogene MYC. Thus, the activation of existing GPR109A in tumor cells coupled with the inhibiting the downregulation of GPA109A is believed to be an effective method to treat cancer.

To test whether GPR109A functions as a tumor suppressor, a human colon cancer cell line which does not express the receptor was transfected with mouse PUMA-G/GPR109A. The re-expression of the receptor alone in this cell line does not do anything to the growth of the cell line. But, following the expression of the receptor, if the receptor is activated with niacin or butyrate, the cells undergo apoptosis. This suggests that tumor cells silence the expression of GPR109A to evade butyrate-induced cell death via the receptor.

One embodiment provides a method for treating cancer by administering to a subject an effective amount of a ligand of GPR109, preferably GPR109A, to promote tumor cell apoptosis optionally in combination with a DNA methylase inhibitor. The composition can be formulated to provide a GPR109 ligand serum level of about 1 to about 1000 µM. A preferred ligand is niacin. A preferred cancer is colon cancer.

These findings are not specific for colon cancer. The expression of the receptor in breast cancer cell lines was also examined. Exactly the same down regulation data was obtained with breast tissue. The expression of GPR109A is reduced markedly in breast cancer cell lines compared to non-transformed cell lines. GPR109B is not affected in breast cancer cell lines. One embodiment provides a method for treating breast cancer by administering an effective amount of ligand for GPR109, preferably GPR109A optionally in combination with a DNA methylase inhibitor.

The data show that re-activation of the expression of GPR109A in cancer tissues has therapeutic potential in the treatment of colon cancer, breast cancer, and leukemias. Agents which might induce the expression of GPR109A in tumor tissues could be potential anti-cancer drugs.

The GPR109B receptor isoform is unique to humans. Its expression is not reduced in cancer. Its ligand specificity is different from that of GPR109A. One of the ligands which has relatively high affinity for GPR109B is the medium-chain fatty acid octanoate. This ligand was used to see if this receptor isoform can be used to kill tumor cells. The data show that this is indeed the case. Two cancer cell lines, a human colon cancer cell line and a human breast cancer cell line were studied. Both these cell lines express GPR109B because the expression of this receptor isoform is not affected in cancer. Treatment of these two cell lines with octanoate leads to apoptosis in a dose-dependent manner. Thus, another embodiment provides a method for treating cancer by administering to a subject an effective amount of a ligand for GPR109B to promote apoptosis in tumor cells optionally in combination with a second therapeutic agent. A preferred ligand is octanoate or a derivative thereof.

Treatment of cancer can be accomplished by administering an effective amount of a DNA methyl transferase inhibitor followed by administering an effective amount of GPR109 ligand. Alternatively, the two drugs can be administered in combination.

B. Inflammatory Disorders

It has been discovered that butyrate is a potent anti-inflammatory agent, and that it elicits its effects by acting as a ligand for GPR109A. Thus, butyrate as well as other ligands for GPR109 can be used to treat one or more symptoms of an inflammatory disorder, preferably an inflammatory disorder of the gut. Representative inflammatory disorders include, but are not limited to inflammatory bowel disease such as Crohn's Disease and Ulcerative Colitis. Additional inflammatory disorders that can be treated include necrotizing enterocolitis and lung inflammation.

The disclosed compositions can be administered to a subject in need thereof in an effective amount to reduce intracellular cAMP, for example in intestinal epithelial cells or lung cells. Reducing intracellular levels of cAMP inhibits signal transduction pathways leading to an inflammatory response.

C. Diarrhea

Compositions including one or more ligands for GPR109A and GPR109B can also be used as anti-diarrheal agents. Since activation of these receptor isoforms decrease intracellular cAMP levels in the colon and intestine, activation of these receptors are believed to enhance electrolyte and water absorption. Compositions including ligands for GPR109A and GPR109B are useful in the treatment of bacteria-induced diarrhea (cholera and Traveler's diarrhea). Thus, one embodiment provides a method for treating diarrhea by administering an effective amount of ligand for GPR109, preferably GPR109A, to reduce intracellular levels of cAMP in intestinal epithelial cells.

IV. Methods of Detection

One embodiment provides a method for detecting or assisting in the diagnosis of inflammatory bowel disease by obtaining a sample from a subject and assaying the sample for expression levels of GPR109, preferably GPR109A. Suitable samples include tissue, cells, blood, or plasma, preferably intestinal tissue. Decreased expression of GPR109 in the sample relative to a control is indicative of inflammatory bowel disease. Methods for detecting the expression of genes or proteins are known in the art.

EXAMPLES

Example 1

Butyrate Elicits its Anti-Inflammatory Effects on Colonic Epithelial Cells via GPR109A The bacterial fermentation product butyrate effectively suppresses the NF-κB promoter activity induced by the bacterial lipopolysaccharide in the normal colonic epithelial cell line CCD841. Several other studies have demonstrated similar anti-inflammatory effects of butyrate in colonic epithelial cells using alternative experimental approaches (Reviewed in Hamer et al. The role of butyrate on colonic function. *Alimentary Pharmacology and Therapeutics* 27: 104-119, 2008). All these studies exposed the colonic epithelial cells to extracellular butyrate and then monitored its anti-inflammatory effects. But, none of these studies has identified the effector molecule that transduces the observed anti-inflammatory effects of extracellular butyrate. A butyrate transporter (SLC5A8) and a butyrate receptor (GPR109A) are present in colonic and intestinal epithelial cells. It is believed that these two proteins mediate the anti-inflammatory effects of butyrate in the intestine/colon in the presence of commensal bacteria. The absence or reduced levels of butyrate in the intestinal/colonic lumen is likely to contribute to the pathogenesis of not only inflammatory bowel disease but also necrotizing enterocolitis.

Figure 1:
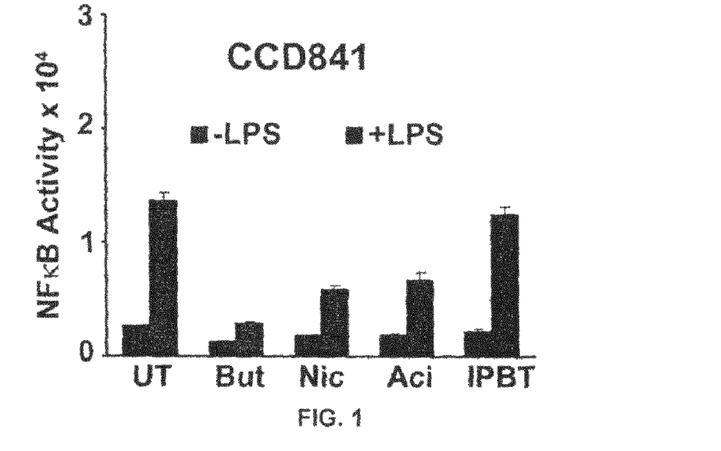
FIG. 1 is a bar graph of NF-κB activity×$10^4$ in CCD841 cells treated with butyrate, nicotinate, acifran, or 1-isopropyl-benzotriazole-5-carboxylic acid) in the presence or absence of lipopolysaccharide.

It has been discovered that the butyrate receptor GPR109A is responsible for the anti-inflammatory effects of butyrate in the intestinal/colonic epithelial cells. The anti-inflammatory effect of butyrate was monitored in colonic cells by its ability to suppress LPS-induced activation of NF-κB promoter with luciferase as the reporter. The participation of SLC5A8 and GPR109A in mediating the effects of extracellular butyrate was differentiated first by using specific ligands. If SLC5A8 is involved in the process, the transporter-facilitated entry of butyrate followed by inhibition of histone deacetylases (HDACs) inside the cells would be responsible for the effects. If GPR109A is involved in the process, the activation of the receptor by extracellular butyrate would be responsible for the effects. Therefore, the effects of butyrate, nicotinate, acifran, and IPBT (1-isopropyl-benzotriazole-5-carboxylic acid) on LPS-induced induction of NF-κB promoter activity were examined in normal human colonic epithelial cell line CCD841. This cell line expresses SLC5A8 as well as GPR109A constitutively. Butyrate and nicotinate are substrates for SLC5A8, but butyrate is an HDAC inhibitor whereas nicotinate is not. Nicotinate and acifran are specific ligands for GPR109A. IPBT is not a ligand for GPR109A but a specific ligand for GPR109B, the human-only isoform of GPR109A. Butyrate, nicotinate, and acifran were able to block LPS-induced activation of NF-κB promoter (FIG. 1; But, butyrate; Nic, nicotinate; Aci, acifran; IPBT, 1-isopropyl-benzotriazole-5-carboxylic acid). In these experiments, cells were first transfected with the construct carrying the NF-κB-luciferase, pretreated with GPR109A ligands (1 mM) for 8 h and then exposed to LPS (100 ng/ml) for 4 h. Following the treatment, cell lysates were used to measure luciferase activity as a read-out for activation of NF-κB. These data show that GPR109A is responsible for the observed effects of extracellular butyrate. In addition, the data show that GPR109B is not involved in this process.

Figure 2A:
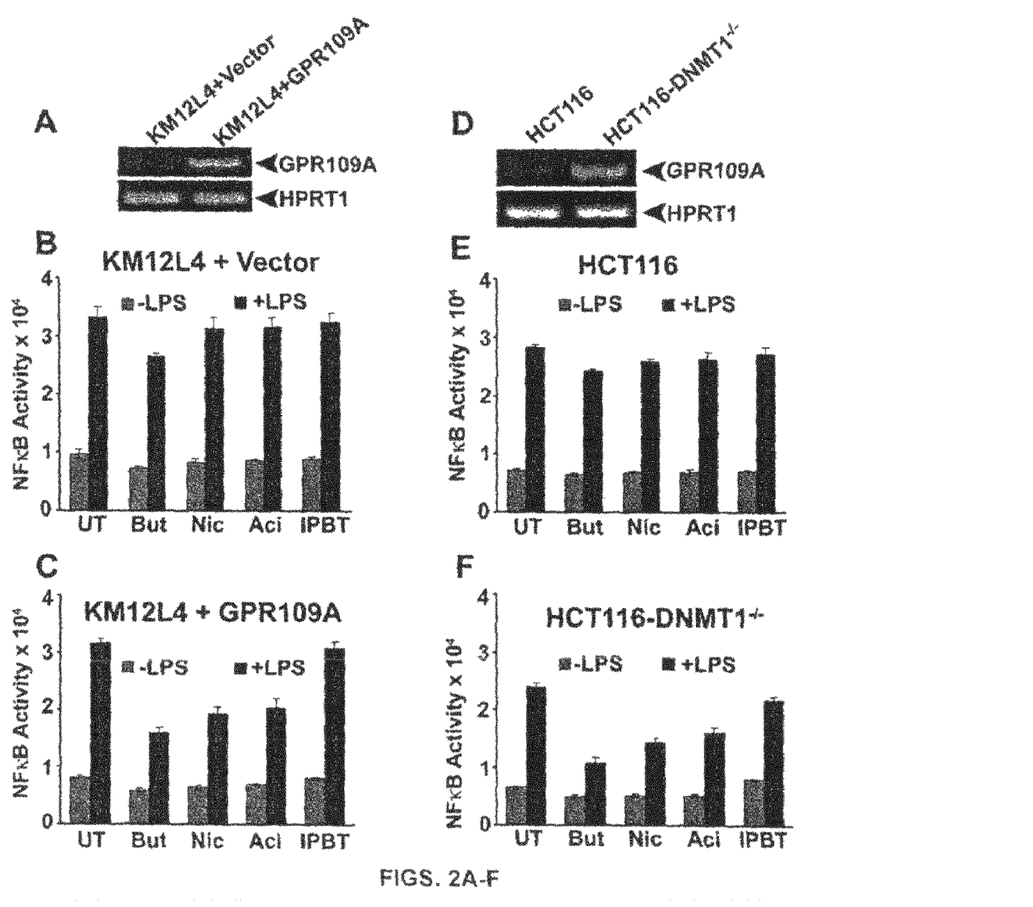
FIG. 2A shows a gel of RT-PCR products of GPR109A or HPRT1 in KM12L4 cells plus vector or KM12L4 cells transfected with GPR109A.

To confirm these findings, the human colon cancer cell line KM12L4 which does not express GPR109A was used. The cells were transfected with either empty vector or human GPR109A cDNA. RT-PCR analysis demonstrated the absence of GPR109A expression in these cells and the expression of the receptor upon transfection with human GPR109A cDNA (FIG. 2A). We cloned the human GPR109A cDNA by RT-PCR using mRNA prepared from human colon, and subcloned the RT-PCR product into pcDNA vector under the control of the cytomegalovirus promoter. The insert was sequenced to confirm its molecular identity. We established its functional identity by evaluating the effects of butyrate and nicotinate in a heterologous expression system. For this, we expressed the receptor in HEK293 cells (a human kidney cell line) which express the G-protein alpha. The activation of the receptor was monitored by measuring the activity of a K+-channel. We confirmed the functional activity of the cloned receptor also by measuring the binding of radiolabeled nicotinate in cells expressing the cloned receptor. We then used the construct to evaluate its role in NF-κB activation using KM12L4 cell line (a human colonic cancer cell line which does not express the receptor constitutively). In vector-transfected cells where there is no expression of GPR109A, nicotinate and acifran, the ligands for the receptor, did not have any effect on LPS-induced activation of NF-κB promoter (FIG. 2B). Butyrate produced a small, but a significant effect. In contrast to these vector-transfected cells, cells with ectopic expression of GPR109A behaved totally differently. Butyrate, nicotinate, and acifran caused a marked suppression of LPS-induced NF-κB promoter activity (FIG. 2C). These cells constitutively express GPR109B, but nonetheless IPBT, the ligand for this isoform, did not have any effect on the reporter activity in vector-transfected cells and in GPR109A cDNA-transfected cells. These data show that the anti-inflammatory effects of butyrate, nicotinate, and acifran are dependent on the expression of GPR109A. The method for treatment in these experiments was similar to that described above.

Additionally, two different isogenic cell lines of the human colon cancer cell line HCT116, one with normal expression of the DNA methyltransferase I(DNMT1) and the other with deletion of the gene coding for the enzyme (HCT116-DNMT1$^{-/-}$) were used. The silencing of GPR109A in colon cancer cells occurs via DNA methylation caused by DNMT1. Therefore, HCT116 cells do not express the receptor, but when DNMT1 is deleted in the same cell line, the receptor is expressed. This is shown in FIG. 2D. These two HCT116 cell lines, one with no expression of GPR109A and the other with the expression of GPR109A were used to examine the effects of butyrate, nicotinate, and acifran on LPS-induced NF-κB promoter activity. Again, in HCT116 cells with no expression of the receptor, none of these compounds had any significant effect on the promoter activity (FIG. 2E). But, the same compounds under identical conditions suppressed LPS-induced promoter activity in HCT116-DNMT1$^{-/-}$ cells. These data confirm the involvement of GPR109A in the anti-inflammatory effects of butyrate and other ligands of the receptor.

Example 2

Butyrate Suppresses Dendritic Cell Maturation via SLC5A8

The development of bone marrow-derived dendritic cells is inhibited by butyrate. Various short-chain fatty acids as well as nicotinate were evaluated for their ability to block the development of dendritic cells. These data showed that butyrate, pyruvate, and propionate were able to block the development whereas acetate and nicotinate had no effect. All of these monocarboxylates are substrates for SLC5A8, but only butyrate, pyruvate, and propionate function inside the cells as HDAC inhibitors. The findings that only those monocarboxylates which function as HDAC inhibitors block the dendritic cell development suggest the involvement of SLC5A8 in the process because if the inhibitors are not taken into the cells via SLC5A8, they would not have any effect. Butyrate and nicotinate are also ligands for the receptor GPR109A, but butyrate is able to block the dendritic cell development whereas nicotinate is not, indicating that GPR109A does not play any role in this process. In these experiments, mouse bone marrow cells were collected and cultured in the presence of various ligands (1 mM) for 4 days. Following this, FACS (fluorescence activated cell sorting) was used to identify the fraction of various immune cell types in the sample.

Example 3

Comparison of GPR109A Expression in the Intestinal Tract Between Conventional Mouse and Germ Free Mouse GPR109A is a G-protein-coupled receptor for butyrate. It is expressed in the small intestine as well as in the colon. The expression is restricted to the lumen-facing apical membrane where the receptor can come in contact with butyrate in the lumen. Butyrate is a fermentation product of commensal bacteria in the intestinal tract. Therefore, the question is whether the presence or absence of bacteria in the intestinal tract would influence the expression of this receptor in the host intestinal tract. If the bacterial metabolite butyrate is the ligand for the receptor, what would happen to the expression of the receptor if the ligand is not there in the intestinal lumen? This question was addressed by comparing the expression of GPR109A in the intestinal tract (ileum and colon, the segments of the intestinal tract which are exposed to significant bacterial colonization) between conventional mouse (which harbors bacteria) and germ free mouse (which does not have any bacteria anywhere in the body). Germ free mice and age-matched conventional mice are commercially available from Taconic. The animals are sacrificed as soon as they arrive. The ileum and colon are collected from these mice and monitored the expression of the receptor by RT-PCR and immunofluorescence. The results show that the expression of GPR109A is markedly reduced in germ free mouse, both in the ileum and colon. This immunofluorescence data correlates with RT-PCR data in the ileum. In the colon, the decrease in mRNA levels was not prominent, but the immunofluorescence data clearly show a marked decrease in protein expression. These data show that the presence of bacteria have marked influence on the expression of the butyrate receptor in the host intestinal tract.

Taken collectively, these new sets of data show that butyrate is a potent anti-inflammatory agent and that it elicits its effects by acting as a ligand for GPR109A. This anti-inflammatory role of butyrate may have relevance to the pathogenesis of inflammatory bowel disease. A recent study has shown that butyrate-producing bacteria are reduced in the intestine of patients with Crohn's disease. The deficiency of butyrate may be a pathogenic factor for Crohn's disease. Butyrate, which acts via GPR109A, suppresses inflammation in the gut and thus has potential as a therapeutic agent for the treatment of inflammatory bowel disease.

Example 4

Figure 3A:
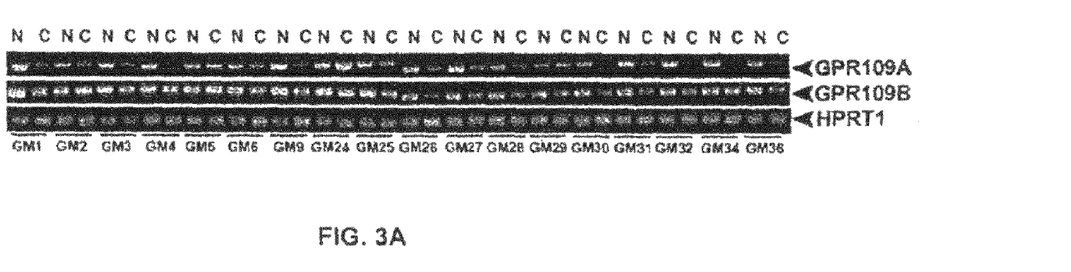
FIG. 3A shows a gel of RT-PCR products of GPR109A, GPR 109B, or HPRT1 in paired normal (N) and cancer (C) specimens from human colorectal cancer patients.
Figure 3B:
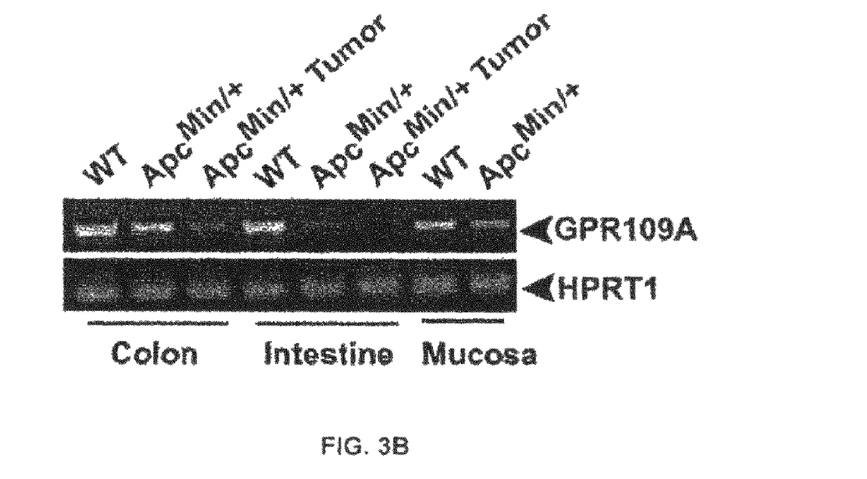
FIG. 3B is a gel showing steady-state levels of mRNAs for GPR109A and HPRT1 in intestinal and colonic tissues from wild type mice and Apc$^{Min/+}$ mice.

Expression of GPR109A and GPR109B in Normal Colon and Silencing of GPR109A in Colon Cancer Semi-quantitative RT-PCR was carried out to monitor the steady-state levels of mRNAs specific for GPR109A and GPR109B mRNA in paired normal (N) and cancer (C) specimens from human colorectal cancer. Representative gels from paired samples of normal colonic epithelium and colon cancer from 18 patients are shown. The patients' serial numbers are given as GM1, GM2, etc (FIG. 3A). Steady-state levels of mRNAs for GPR109A and HPRT1 in intestinal and colonic tissues from wild type mice and Apc$^{Min/+}$ mice are shown in FIG. 3B. Immunofluorescence analysis of GPR109A protein expression was conducted on intestinal and colonic tissues from wild type mice and Apc$^{Min/+}$ mice. De-paraffinised tissue sections were treated with anti-GPR109A antibodies followed by fluorophore-conjugated anti-rabbit IgG secondary antibody (red fluorescence). DAPI was used for nuclear staining (blue fluorescence). Inserts represent 400× magnification. These experiments showed the following: (a) the expression of GPR109A is markedly reduced in colon cancer in humans whereas the expression of GPR109B is not altered appreciably; (b) the decreased expression of GPR109A is also seen the mouse model of intestinal/colon cancer; (c) the decreased levels of GPR109A mRNA are accompanied with corresponding decreased levels of GPR109A protein in the animal model.

Example 5

DNMT1-Specific Epigenetic Silencing of GPR109A in Colon Cancer

Figure 4A:
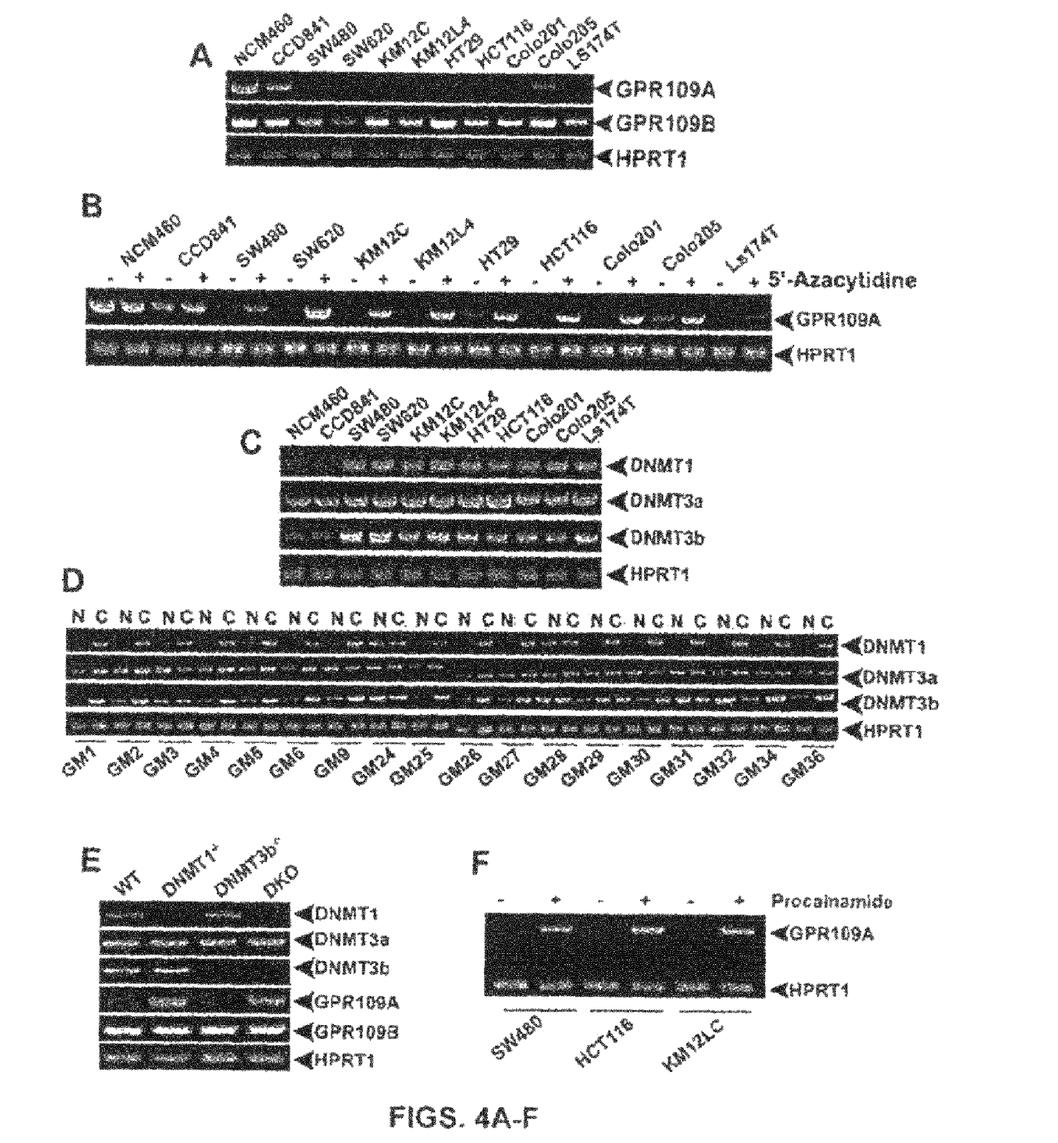
FIG. 4A shows steady-state levels of mRNAs for GPR109A, GPR109B, and HPRT1 in two normal human colon cell lines (NCM460 and CCD841) and nine human colon cancer cell lines (SW480, SW620, KM12C, KM12L4, HT29, HCT116, Colo201, Colo205, and Ls174T).

FIG. 4A shows steady-state levels of mRNAs for GPR109A, GPR109B, and HPRT1 in two normal human colon cell lines (NCM460 and CCD841) and nine human colon cancer cell lines (SW480, SW620, KM12C, KM12L4, HT29, HCT116, Colo201, Colo205, and Ls174T). FIG. 4B shows semi-quantitative RT-PCR for GPR109A mRNA in normal colon (NCM460 and CCD841) and colon cancer (SW480, SW620, KM12C, KM12L4, HT29, HCT116, Colo201, Colo205, and Ls174T) cell lines after treatment with or without 5'-azacytidine (2 µg/ml; 72 h). HPRT1 mRNA was used as an internal control. FIG. 4C shows steady-state levels of DNMT1, DNMT3a, and DNMT3b mRNA in normal colon cell lines and cancer colon cell lines. FIG. 4D shows up-regulation of DNMT1 and DNMT3b in human colon cancer. Steady-state levels of mRNAs for DNMT1, DNMT3a, DNMT3b, and HPRT1 were monitored in normal human colon tissues and in human colon cancer tissues by semi-quantitative RT-PCR. FIG. 4F shows the correlation between expression levels of DNMT1, DNMT3a, and DNMT3b mRNA and expression levels of GPR109A and GPR109B mRNA in HCT116 cell line (a human colon cancer cell line) and in isogenic cell lines with the deletion of DNMT1, DNMT3b, or both (DKO). FIG. 4F shows an obligatory role for DNMT1 in the cancer-associated silencing of GPR109A. Three different colon cancer cell lines were treated with procainamide, a specific inhibitor of DNMT1, and the expression of GPR109A was monitored in cells treated with or without the inhibitor.

These studies have shown the following: (a) GPR109A is expressed in normal human colonic epithelial cell lines whereas the expression is markedly reduced or completely absent in nine different human colon cancer cell lines; (b) the silencing of GPR109A expression in cancer cell lines involves DNA methylation because treatment of the cancer cell lines with 5'-azacytidine, a pan-inhibitor of DNA methylation, re-activates the expression of the receptor; (c) DNMT1 and DNMT3b are upregualted in primary colon cancer in humans and also in several human colon cancer cell lines; (d) it is the DNMT1 isoform of DNA methyltransferase which is responsible for the cancer-associated silencing of GPR109A.

Example 6

Figure 5A:
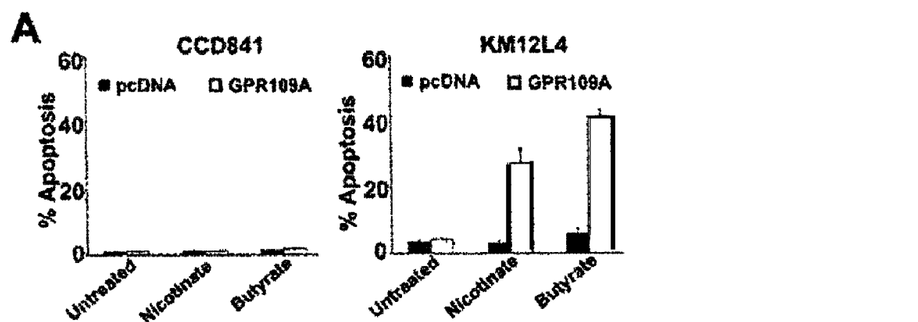
FIG. 5A shows a pair of bar graphs of percent apoptosis in CCD841 (a normal human colonic epithelial cell line) and KM12L4 (a human colon cancer cell line) cells transfected with pcDNA or GPR109A cDNA. Twenty four hours following transfection, cells were treated with pyruvate or butyrate (0.5 mM) for 24 h, and cells were collected and fixed with 50% ethanol and stained with propidium iodide. Apoptotic cells (sub-01 populations) were analyzed by FACS.
Figure 5B:
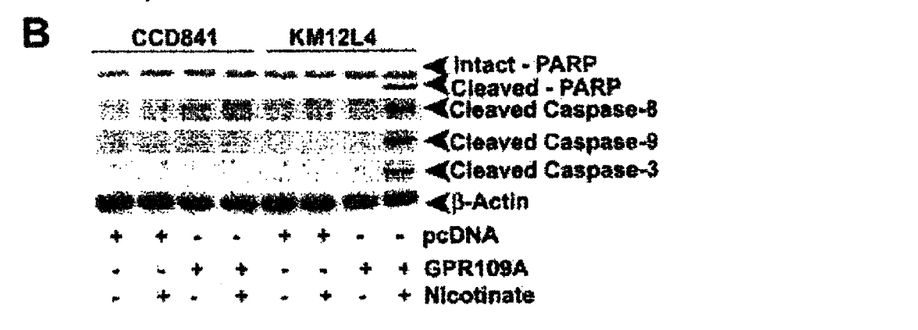
FIG. 5B is a Western Blot of cell lysates, prepared from CCD841 and KM12L4 cells, which were transfected with pcDNA or GPR109A cDNA and then treated with or without nicotinate, were resolved by SDS-PAGE electrophoresis and the membranes were analyzed for PARP cleavage and activation of various caspases using appropriate antibodies specific for each of the caspases. β-Actin was used as a loading control.

Ectopic Expression of GPR109A Induces Tumor Cell-Specific Apoptosis in Human Colon Cell Lines in a Ligand-Dependent Manner FIG. 5A shows CCD841 (a normal human colonic epithelial cell line) and KM12L4 (a human colon cancer cell line) cells transfected with pcDNA or GPR109A cDNA. Twenty four hours following transfection, cells were treated with pyruvate or butyrate (0.5 mM) for 24 h, and cells were collected and fixed with 50% ethanol and stained with propidium iodide. Apoptotic cells (sub-G1 populations) were analyzed by FACS. In FIG. 5B cell lysates, prepared from CCD841 and KM12L4 cells, which were transfected with pcDNA or GPR109A cDNA and then treated with or without nicotinate, were resolved by SDS-PAGE electrophoresis and the membranes were analysed for PARP cleavage and activation of various caspases using appropriate antibodies specific for each of the caspases. β-Actin was used as a loading control.

Figure 5C:
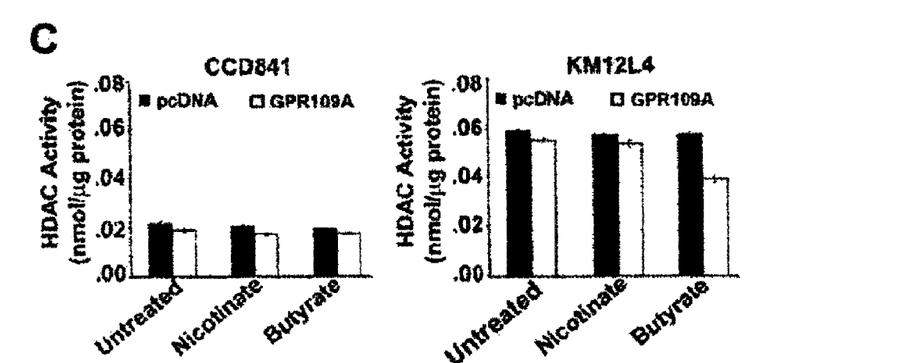
FIG. 5C is a pair of bar graphs of HDAC activity (nmol/µg protein) in CCD841 and KM12L4 cell lines transfected with either pcDNA or GPR109A, and then treated with or without nicotinate or butyrate.
Figure 5D:
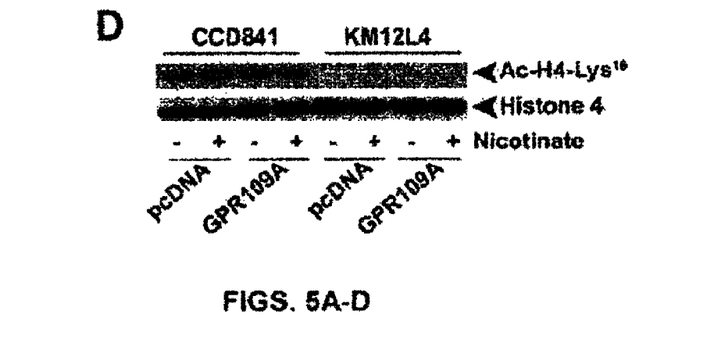
FIG. 5D is a Western blot carried out with these protein samples using antibodies against histone H4 and acetylated histone H4 (Lys 16).

CCD841 and KM12L4 cell lines were transfected with either pcDNA or GPR109A, and then treated with or without nicotinate or butyrate as mentioned above. Cell lysates were prepared from these cells and the HDAC activity was measured using the commercially available HDAC assay kit (FIG. 5C). Western blot analysis was carried out with these protein samples using antibodies against historic H4 and acetylated histone H4 (Lys16) (FIG. 5D).

These experiments show that activation of GPR109A leads to apoptosis specifically in cancer cells, without having any deleterious effect on normal cells. The cancer cell-specific cell death involved caspase activation but does not involve HDAC inhibition.

Example 7

Figure 6A:
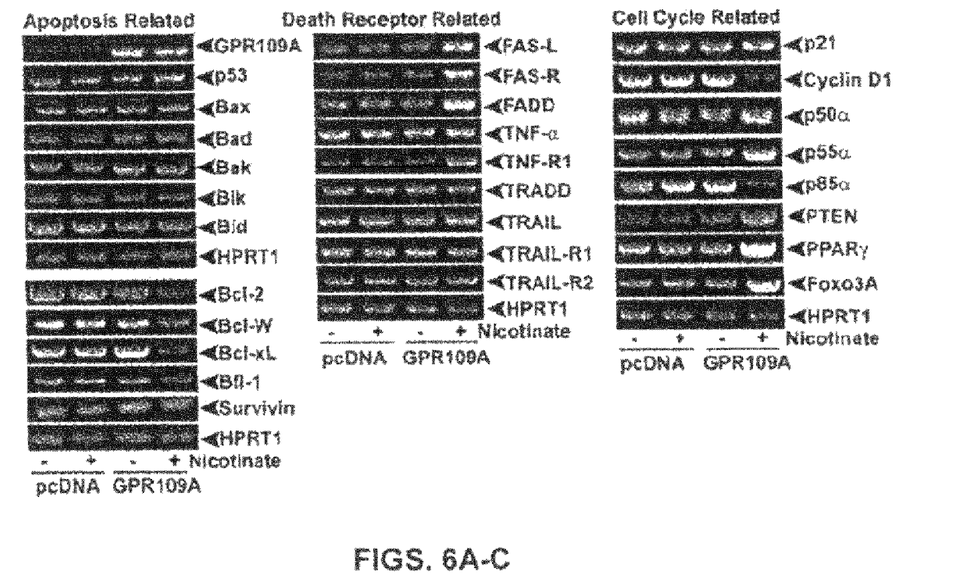
FIG. 6A shows RNA levels for the identified apoptosis-related genes in KM12L4 cells transfected with either pcDNA or GPR109A cDNA, followed by treatment with or without nicotinate (0.5 mM) for 24 h.

Differential Regulation of Apoptotic Signaling by GPR109A/Nicotinate in Human Colon Cancer Cells KM12L4 cells were transfected with either pcDNA or GPR109A cDNA, followed by treatment with or without nicotinate (0.5 mM) for 24 h. Total RNA was extracted from these cells and semi-quantitative RT-PCR was carried out using primers specific for the apoptosis-related genes, death receptor-related genes, and cell cycle-related genes as described above (FIGS. 6A-C). KM12L4 is a human colon cancer cell line which does not express GPR109A constitutively. Therefore, vector-transfected cells when treated with or without nicotinate do not exhibit any change in the expression of various genes involved in apoptosis and cell cycle. This agrees well with previous data that the cells do not undergo apoptosis under these conditions. In contrast, when GPR109A is expressed in these cells by transfection of GPR109A cDNA, exposure of the cells to nicotinate causes marked effects on the expression of various genes involved in apoptosis and cell cycle. Such changes do not occur when these cells were not exposed to nicotinate, indicating that it is the activation of the receptor, not the receptor by itself, which is responsible for the observed changes. Activation of the receptor in these cancer cells decreases the expression of several anti-apoptotic genes, increased the expression of several pro-apoptotic genes, and also suppresses the expression of cell cycle promoters. In addition, the expression of PTEN, a tumor suppressor, is also increased by GPR109A activation. There is also a differential effect on the expression of the various subunits of phosphatidylinositol 3-kinase, with downregulation of p85α expression and upregulation of p50α and p55α expression.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

Example 8

Killing of Colon Cancer Cells with Octanoate, a Ligand for GPR109B

Figure 7:
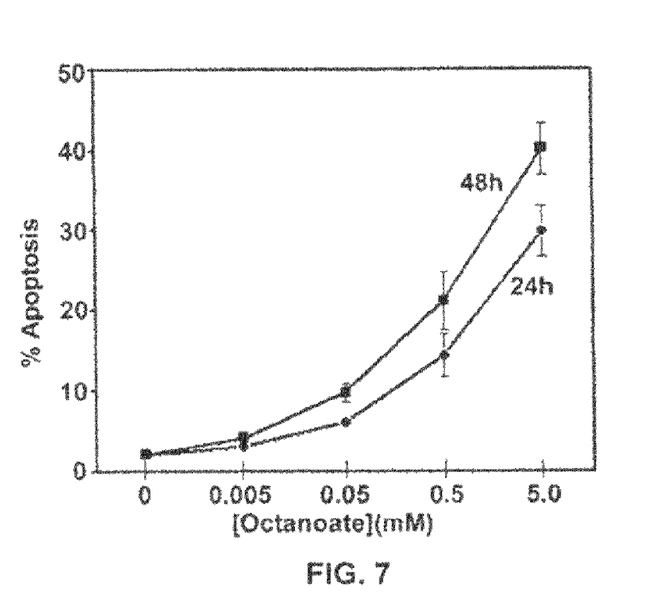
FIG. 7 is a line graph of percent apoptosis versus octanoate (mM) of SW480 cells treated with the indicate concentration of octanoate for 24 hours (●) or 48 hours (■).

Colon cancer cell line SW480 was cultured in the presence of varying concentrations of octanoate for 24 or 48 h, and then cells were fixed in ethanol, stained with propidium iodide, and subjected to FACS analysis to determine the percent of cells undergoing apoptosis. Sub G0/1 cells were quantitated using Cell Quest program and values are expressed as mean+ SEM. The studies showed that treatment of the cancer cells with this GPR109B ligand induced apoptosis (FIG. 7).

We claim:

1. A pharmaceutical composition comprising an effective amount of a ligand for GPR109B to decrease intracellular cAMP levels of a subject in combination with an effective amount of a DNA methylase inhibitor to reduce or inhibit downregulation of GPR109B in the intestinal epithelial cells of the subject relative to a control.

2. The pharmaceutical compositions of claim 1 wherein the DNA methylase inhibitor is selected from the group consisting of 5-azacytidine, 5-aza-2'-deoxytidine, 1-β-D-arabinfurnosyl-5-azacytosine and dihydro-5-azacytidine.

3. The pharmaceutical composition of claim 1 wherein the ligand for GPR109B is in an amount effective to produce a serum blood level of about 1 to about 1000 µM.

4. The pharmaceutical composition of claim 1 comprising a dosage of 0.001 to 100 mg/kg of body weight.

5. The pharmaceutical composition of claim 1 in a unit dosage formulation.

6. The pharmaceutical composition of claim 1 wherein the ligand is octanoate.

7. A method for treating one or more symptoms of cancer comprising administering to a subject an effective amount DNA methyltransferase inhibitor to induce expression of GPR109B in the subject and subsequently administering an effective amount of a GPR109B ligand to promote apoptosis of the cells induced to express GPR109B.

8. The method of claim 7 wherein the ligand is selected from the group consisting of octanoate and derivatives thereof and the DNA methyltransferase inhibitor is selected from the group consisting of 5-azacytidine, 5-aza-2'-deoxytidine, 1-β-D-arabinfurnosyl-5-azacytosine and dihydro-5-azacytidine.

9. The method of claim 7 wherein the cancer is selected from the group consisting of colon cancer, breast cancer, and leukemia.

10. A method for treating an inflammatory disorder comprising administering to a subject an effective amount of a GPR109B ligand to reduce intracellular cAMP in the subject.

11. The method of claim 10 wherein the inflammatory disorder is selected from the group consisting of inflammatory bowel disease, necrotizing enterocolitis and lung inflammation.

12. The method of claim 11 wherein the inflammatory bowel disease is Crohn's or ulcerative colitis.

13. A method for treating diarrhea comprising administering to a subject an effective amount of a GPR109B ligand to decrease intracellular cAMP levels in intestinal epithelial cells of the subject.

14. The method of claim 13 wherein the GPR109B ligand is selected form the group consisting of octanoate and derivatives thereof.

15. A method for inducing expression of GPR109 comprising administering to a subject an effective amount DNA methyltransferase inhibitor to induce expression of GPR109 in the subject and subsequently administering an effective amount of a GPR109 ligand to promote apoptosis of the cells induced to express GPR109.

16. A method for treating one or more symptoms of cancer comprising
- detecting the levels of GPR109 in a sample from a subject,
- administering to a subject with low levels of GPR109 an effective amount of DNA methyltransferase inhibitor to induce expression of GPR109 in the subject, and
- subsequently, administering an effective amount of a GPR109 ligand to promote apoptosis of the cells induced to express GPR109.

* * * * *